(12) United States Patent
Chen et al.

(10) Patent No.: US 9,301,984 B2
(45) Date of Patent: Apr. 5, 2016

(54) LACTOBACILLUS REUTERI GMNL-263 COMPOSITION FOR CONTROLLING BODY WEIGHT AND ITS USE THEREOF

(71) Applicant: GenMont Biotech Inc., Tainan County (TW)

(72) Inventors: Yi-Hsing Chen, Tainan (TW); Feng-Ching Hsieh, Pingtung County (TW); Po-Yung Chen, Tainan County (TW)

(73) Assignee: GenMont Biotech Inc., Tainan County (TW)

( * ) Notice: Subject to any disclaimer, the term of this patent is extended or adjusted under 35 U.S.C. 154(b) by 0 days.

(21) Appl. No.: 14/693,129

(22) Filed: Apr. 22, 2015

(65) Prior Publication Data
US 2015/0250836 A1 Sep. 10, 2015

Related U.S. Application Data (63) Continuation-in-part of application No. 14/152,236, filed on Jan. 10, 2014, now abandoned.

(51) Int. Cl.
| | | |
|---|---|---|
| *A01N 63/00* | (2006.01) |
| *A61K 35/747* | (2015.01) |
| *A61K 45/06* | (2006.01) |
| *A23L 1/29* | (2006.01) |
| *A23L 1/30* | (2006.01) |
| *A61K 35/741* | (2015.01) |
| *A61K 35/745* | (2015.01) |
| *A23K 1/00* | (2006.01) |
| *A61K 35/00* | (2006.01) |

(52) U.S. Cl.
CPC .............. *A61K 35/747* (2013.01); *A23K 1/008* (2013.01); *A23K 1/009* (2013.01); *A23L 1/293* (2013.01); *A23L 1/3014* (2013.01); *A23L 1/3016* (2013.01); *A61K 35/741* (2013.01); *A61K 35/745* (2013.01); *A61K 45/06* (2013.01); *A23V 2002/00* (2013.01); *A61K 2035/115* (2013.01)

(58) Field of Classification Search
CPC ..................................................... A61K 35/747
See application file for complete search history.

(56) References Cited

U.S. PATENT DOCUMENTS

2012/0183504 A1* 7/2012 Lu et al. ........................ 424/93.3

* cited by examiner

*Primary Examiner* — Albert Navarro
*Assistant Examiner* — Mark Navarro
(74) *Attorney, Agent, or Firm* — WPAT, P.C.; Anthony King (57) ABSTRACT

Present invention features a method for controlling body weight, comprising *Lactobacillus reuteri* GMNL-263 with the deposition numbers of BCRC 910452 and CCTCC M 209263. Moreover, the invention also relates to a novel use of the composition or the isolated *Lactobacillus* strain for controlling body weight, whose mechanism is inhibiting biosynthesis of lipids and reducing formation of lipid droplets so as to control body weight.

10 Claims, 6 Drawing Sheets

Fig. 8

LACTOBACILLUS REUTERI GMNL-263 COMPOSITION FOR CONTROLLING BODY WEIGHT AND ITS USE THEREOF

CROSS-REFERENCE TO RELATED APPLICATIONS

This application is a Continuation-in-Part of application Ser. No. 14/152,236, filed on Jan. 10, 2014, and now for which the benefit is claimed under 35 U.S.C §120; the content of each of the abovementioned patent application is hereby incorporated by reference herein in its entirety and made a part of this specification.

BACKGROUND OF THE INVENTION

1. Field of the Invention

The present invention features an isolated *Lactobacillus* strain and its use for controlling body weight.

2. Description of the Prior Art

With the development of cities, obesity has gradually become the health killer in modern life nowadays. Accumulated studies also indicate obesity increases the risk of developing diabetes, cancers, gall bladder diseases, high blood pressure as well as atherosclerosis, and therefore effectively reducing body fat and decreasing obesity are urgent tasks.

Obesity is usually caused by excess body fat accumulated in the body due to physiological or biochemical functional change(s) and can have adversely affected the health. Lipids commonly include fats, phospholipid and cholesterol. The increase of weight is mainly due to the fact that total energy intake is more than energy expenditure. In general, obesity can be divided into two types including simple obesity and second obesity. Simple obesity can be further classified as idiopathic obesity and acquired obesity and account for nearly 95% of obesity. Idiopathic obesity is caused by huge numbers of adipocytes and is usually found in children obesity. Meanwhile, acquired obesity results from larger adipocytes and is more common in adults with obesity problems. Second obesity is also called symptomatic obesity and is often the result of endocrine or metabolic diseases. Obesity has been found to correlate with certain chronic diseases such as diabetes, high blood pressure, stroke, biliary calculus, gout and certain cancers.

Currently, five strategies are available for treating obesity: diet, exercise, behavioral therapy, drug therapy and therapeutic operation. Different treatment or combinations of these treatments are selected for treating patients with obesity based on the risk factors in the patient's health, the rate of weight loss as well as the corresponding effects of those treatments. The rate of weight loss and the effects are determined according to various factors such as age, height, family history and risk factors, etc. The mechanisms of drug therapy include appetite, increase energy consumption, stimulate lipid transfer, reduce triacylglycerol synthesis and inhibition of lipid adsorption. The common drugs used clinically for treatment are phenylpropanolamine (PPA), orlistat/Xenical™, and sibutramine/Reductil™. Nonetheless, treating obesity with natural materials instead of using drugs has become the new trend recently.

Probiotics is beneficial to the health of gastrointestinal tract, and several reports have indicated that in addition to regulating immune functions, these bacteria can also help ameliorate disease symptoms such as high blood pressure, cancers and high cholesterol. Moreover, studies have demonstrated certain probiotic bacteria can regulate the body weight and body fat of obese mice, regardless of the status of these bacteria, live or dead. From prior research, it is speculated that probiotics may contain crucial effective ingredient(s). In prior application, U.S. Pat. No. 8,298,526, the inventor of present invention discovered *Lactobacillus reuteri* GMNL-263 can effectively improve the symptoms of type I diabetes. However, whether probiotics can efficiently improve obesity symptoms or reduce weight and through which mechanism(s) remain unclear due to the limited literature available up to date.

In previous examination, the examiner mentioned that the result of instant case was inherently achieved by US20120183504 and U.S. Pat. No. 8,298,526 given that the identical composition was administered and would necessarily achieved the same result, given that it was the identical composition.

Figure 2A:
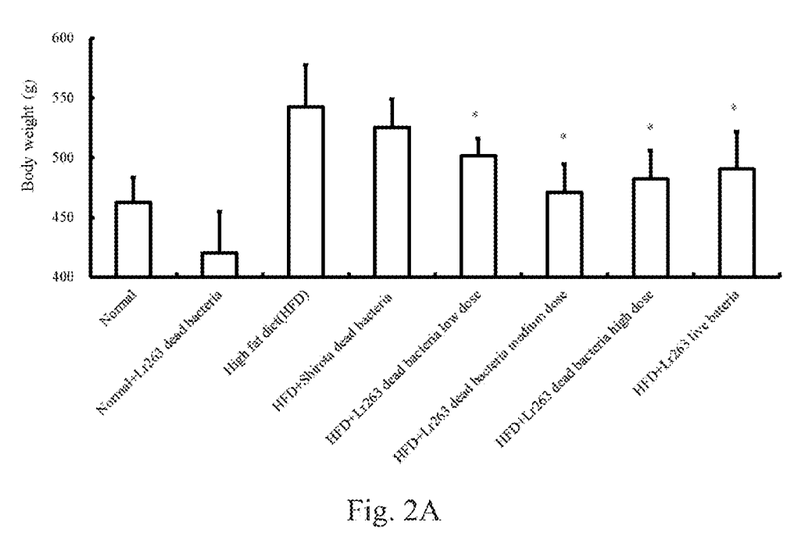
FIG. 2A shows the effects of Lr263 bacteria on body weight at the week 12.

In the present continuation-in-part, the applicant provided new matters demonstrating the efficiency of lowering weight and fat is better treating with dead bacteria than live bacteria if the dosage is the same. Moreover, according to the examples, the effect can be achieved with the dosage between $5 \times 10^5$ and $2 \times 10^{10}$ cells/ml (dead bacteria). Compare to the references, U.S. Pat. No. 8,298,526 discloses the effect of live bacteria $2 \times 10^{10}$ cfu/day for improving diabetes, and US20120183504 discloses the effect of bacteria $10^9$ organism/rat/day for improving renal fibrosis (US20120183504 mentions that the bacteria can be treated live or inactive; however, there are no comparison between the effect of live bacteria and live bacteria in the example, and the example only provides the effect of treating live bacteria). After the restriction in the instant case, the claims were restricted to dead bacteria and dosage of bacteria. Neither U.S. Pat. No. 8,298,526 nor US20120183504 disclosed the novel effect of lowering weight and fat by administrating dead bacteria and its dosage as disclosed in the instant case. In addition, in US20120183504 the body weight of rats of normal group did not decrease after administrating bacteria (US20120183504 FIG. 1, 2); on the contrary, in the instant case the body weight of rats of normal group significantly lowered down after administrating dead bacteria (FIG. 2A). This suggests the mechanism and effect are different between the instant case and US20120183504. Therefore, the different result implies that the effect of the instant invention is distinct from US20120183504 and the instant case should be considered as a novel invention that requires laborious experimentation to acquire unexpected results.

In view of the above, one of ordinary skills in the art would not be able to practice the current application by the teachings of the prior art.

SUMMARY OF THE INVENTION

While only limited studies are available on the identification of the relations between the abovementioned probiotic bacteria and obesity, searching for probiotic bacteria that efficiently improves the symptoms of obesity is a critical task. Since 3T3-L1 preadipocytes has been widely used in studying adipose tissues and relevant mechanisms, these cells are selected herein to examine the effects of *Lactobacillus* bacterial cell lysates on biosynthesis of adipocytes and *Lactobacillus reuteri* GMNL-263(Lr263) has been identified as a potential bacterial strain for treating obesity. Further animal studies were conducted in the obese mice to investigate the effects of this newly identified strain by feeding model mice with high fat food and different dosages of live or dead Lr263 bacteria.

In one aspect, present invention provides a method for reducing or maintaining body weight, comprising of administrating a probiotic composition, wherein the probiotic bacterial strain includes *Lactobacillus reuteri* GMNL-263 with the deposition numbers of BCRC 910452 and CCTCC M 209263.

According to the invention, the abovementioned *Lactobacillus reuteri* GMNL-263 composition further comprises of at least one of the following ingredients: live bacteria, dead bacteria and cell lysates.

Based on the invention, the aforementioned composition is a pharmaceutical composition, food, or food composition, wherein the pharmaceutical composition further includes a pharmaceutically acceptable vehicle, wherein the pharmaceutical composition is a dosage form for oral administration and the dosage form is selected from the following list or their combinations thereof, but is not limited to, solution, suspension, emulsion, powder, tablet, pill, lozenge, troche, chewing gum, slurry, capsule and other suitable forms, wherein the pharmaceutical composition contains at least one type of the following cells: a daily dose of $10^5$ to $10^{10}$ live or dead GMNL-263 bacteria, wherein the food further contain at least one of the following probiotic bacteria: *Lactobacillus* sp., *Bifidobacterium* sp., *Streptococcus* sp., and yeast. The food also contain an edible material and said edible material includes, but is not limited to, water, fluid milk products, milk, concentrated milk, fermented milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jelly, candies, infant formulas, health foods, animal feeds, Chinese herbs, dietary supplements, and the like, wherein the food comprises at least one of the following cell types: a daily dose containing $10^5$ to $10^{10}$ of live or dead GMNL-263.

In another aspect, present invention provides a use of the abovementioned composition for manufacturing the composition used for treating obesity and relevant complications, wherein the complications are selected from the following diseases, but are not limited to, hyperlipidemia, atherosclerosis, coronary heart disease and fatty liver, or their combinations thereof.

According to a further aspect, present invention also provides a use of the abovementioned composition for manufacturing the composition used for inhibition of lipid biosynthesis, high total body fat, high visceral fat, high gonadal fat, high total cholesterol, high triglyceride (TG) concentration, or the ratio of low density lipoprotein and high density lipoprotein (LDL/HDL).

In another aspect, the present invention provides a method for the treatment of obesity and its relevant complications, comprising of administrating the aforementioned composition.

In one aspect, the invention provides a method for the treatment of inhibiting lipid biosynthesis, high total body fat, high visceral fat, high gonadal fat, high total cholesterol, high triglyceride (TG) concentration, or the ratio of low density lipoprotein and high density lipoprotein (LDL/HDL), comprising of administrating the aforementioned composition.

In another aspect, the present invention provides a composition for the treatment of treating obesity and its relevant complications, comprising of administering the aforementioned composition.

In one aspect, the invention provides a composition for the treatment of inhibiting lipid biosynthesis, high total body fat, high visceral fat, high gonadal fat, high total cholesterol, high triglyceride (TG) concentration, or the ratio of low density lipoprotein and high density lipoprotein (LDL/HDL), including the aforementioned composition.

These features and advantages of the present invention will be fully understood and appreciated from the following detailed description of the accompanying drawings.

DETAILED DESCRIPTION OF THE PREFERRED EMBODIMENT

Unless defined otherwise, all technical and scientific terms used herein have the meaning commonly understood by a person skilled in the art to which this invention belongs. The present invention will now be described more specifically with reference to the following embodiments, which are provided for the purpose of demonstration rather than limitation.

The invention features a composition used for treating obesity, which includes *Lactobacillus reuteri* GMNL-263 with the deposition numbers of BCRC 910452 and CCTCC M 209263. In addition, present invention also relates to a novel use of the composition or the *Lactobacillus* bacterial strain for treating obesity, and the mechanism of inhibiting lipid biosynthesis so as to reduce formation of lipid droplets and treat obesity.

The *Lactobacillus* isolated strain also includes the progeny obtained from the subculture of the *Lactobacillus* strain or its mutants, which still preserve the same features, genomes or use (for inhibition of enterovirus) of the bacterial strain disclosed in the invention.

The inventive composition includes, but not is limited to, foods, beverages, health foods, additives in animal drinking water, animal feed additives, pharmaceutical compositions for animals and human beings, food additives, beverage additives and the like.

As used herein, the following terms have the meanings ascribed to them unless specified otherwise.

The term "treatment", "under treatment" and similar terms refer to the methods which ameliorate, improve, reduce or reverse the patient's disease or any relevant symptoms caused by the disease, or methods which can prevent the onset of such diseases or any resulting symptoms.

The term "pharmaceutically acceptable" is used to describe substances used in the composition which must be compatible with other ingredients in the formulation and be harmless to the subject.

The term "cell lysate" is used herein refers to a single cell lysate obtained from particular cell lysis procedures or a series of cell lysis procedures, or the cell lysate may also be a combination of several cell lysates obtained from independent cell lysis procedures. The compositions revealed in the invention therefore are included in the term "cell lysate".

The inventive composition can be prepared into a dosage form for suitable application of the inventive composition by using technology commonly understood by a person skilled in the art through formulating the above mentioned *Lactobacillus* isolated strain(s) with a pharmaceutically acceptable vehicle, wherein the excipients include, but are not limited to, solution, emulsion, suspension, powder, tablet, pill, lozenge, troche, chewing gum, capsule and other suitable forms.

The pharmaceutically acceptable vehicle may contain one or several reagents selecting from the following list: solvent, emulsifier, suspending agent, decomposer, binding agent, excipient, stabilizing agent, chelating agent, diluent, gelling agent, preservative, lubricant, surfactant and other agents suitable for use in the invention.

In the abovementioned compositions, one or more dissolving aids, buffers, preservatives, colorants, fragrances, flavoring agents and the like, which are commonly used for formulation can be added as desired.

In one preferred embodiment, an edible material can be further added to the inventive composition for preparation of food or health products. Said edible material may include, but is not limited to, water, fluid milk products, milk, concentrated milk, fermented milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jellies, candies, infant formulas, health foods, animal feeds, Chinese herbs, dietary supplements, and the like.

Additionally, the novel bacterial strain identified in the present invention can also be included in a composition containing other conventional bacterial strains.

The inventive composition may further comprise of at least one probiotic bacterial strain selected from the group consisting of *Lactobacillus* sp., *Streptococcus* sp., *Bifidobacterium* sp., and yeasts.

Said conventional *Lactobacillus* sp. include, but are not limited to, *Lactobacillus lactis*, *Lactobacillus acidophilus*, *Lactobacillus helveticus*, *Lactobacillus bifidus*, *Lactobacillus casei*, *Lactobacillus paracasei* subsp. *paracasei*, *Lactobacillus rhamnosus*, *Lactobacillus gasseri*, *Lactobacillus reuteri*, *Lactobacillus fermentum*, or their combinations thereof.

Said conventional *Streptococcus* sp. include, but are not limited to, *Streptococcus lactis*, *Streptococcus thermophilus*, *Streptococcus cremoris*, or their combinations thereof.

Said conventional *Bifidobacterium* sp. include, but are not limited to, *Bifidobacterium breve*, *Bifidobacterium lactis*, *Bifidobacterium longum*, *Bifidobacterium bifidum*, or their combinations thereof.

Said conventional yeasts include, but are not limited to, *Saccharomyces cereviseae*, *Candida kefyr*, *Saccharomyces florentinus*, or their combinations thereof.

In another aspect, present invention provides the method or use of the composition prepared for reducing or maintaining body weight by using the aforementioned *Lactobacillus* bacteria.

The administration routes of the composition and the method for reducing or maintaining body weight which was disclosed in the invention can be adjusted accordingly based on the needs and has no special restrictions, and oral administration of suitable dosage forms of the composition is the preferred route for administering the inventive composition.

The present invention will now be described more specifically with reference to the following embodiments, which are provided for the purpose of demonstration rather than limitation. The drugs as well as biomaterials used in the invention are all commercially available materials and the sources disclosed below are merely examples.

The inventor (GenMont Biotech Inc.) of this application isolated more than 100 bacterial isolated strains from the gastrointestinal tract of healthy adults, which allows establishment of the culture collection of the invention. The collection locations, collection times, collectors as well as contact information of the collectors are summarized in the Table 1.

TABLE 1

Genetic Resources Information

| | Source of the collected genetic information | Collection time (yyyy/mm/dd) | Collection location (Province City) | Collector (Name) | Contact information of the collector |
|---|---|---|---|---|---|
| GMNL-263 | Healthy adult Gastrointestinal tract | Jan. 20, 2006 | Taiwan Tainan City | Wang, Yin-Yu | No. 8, Nanke 7th Road, Shanhua District, Tainan City |

The deposition numbers, deposition date and names of the *Lactobacillus* strains which can be used for treating obesity are selected and summarized in Table 2. Among which, *Lactobacillus reuter* GMNL-263(Lr263) is a previously reported strain and the original copies of documents as well as relevant information including strain characteristics, proof of deposition and viability test reports can all be found in a number of international patents.

TABLE 2

China Center for Type Culture Collection (CCTCC) deposition information of the *Lactobacillus* strains of the invention.

| Name of the strain | Deposition number | Deposition date | Disclosed information in patents |
|---|---|---|---|
| *Lactobacillus reuteri* | CCTCC M GMNL-263 209263 | Nov. 13, 2009 | TW I340021 U.S. Pat. No. 8,298,526 B2 JP 5185976B TW I355939 |

China Center for Type Culture Collection (CCTCC) address: Hongshan Qu Ba Yi Avenue, Wuhan, Hubei, 430072, P.R.C.

EXAMPLE 1

Materials: 3T3-L1preadipocytes (BCRC 60159 purchased from Food Industry Research and Development Institute), DMEM-high glucose and MRS broth.

Methods: The technique utilized herein is modified from which disclosed in the previous study of Park et. al. (2011).

a. Preparation of *Lactobacillus* Bacterial Cell Lysate:
  1. Bacterial strains were obtained from the culture collection and incubated in MRS broth for 18 hrs.
  2. The bacterial cultures were centrifuged at 2,700 rpm for 10 minutes, washed with PBS and the broth was discarded for collection of the bacterial strains without medium.
  3. The collected bacteria were re-suspended with PBS and adjusted to the concentration of $1 \times 10^{10}$ cell/ml.

The adjusted bacterial culture was subjected to sonication for lysis and then filtered with a 0.22 μm filter membrane before stored at −20° C.

b. In vitro Cell Culture of 3T3-L1 Cells:
  1. 3T3-L1 adipocytes were cultured in DMEM-high glucose medium supplemented with 10% fetal bovine serum (FBS) and 1% penicillin and streptomycin (PS) and the medium was changed every 2-3 days when sub-culturing the cells.
  2. The cells were inoculated onto 24-well plates at the concentration of $8 \times 10^4$ cells/well and confluent growth shall be obtained after 3-day culture. The medium was then replaced and the cells were cultured for additional two days.
  3. The medium was then replaced with DMEM-high glucose containing 10% FBS, 10 μg/mL insulin, 0.5 mM 3-isobutyl-1-methylxanthine and 1 μM dexamethasone, and the cells were cultured for additional three days.
  4. At the end of 3-day culture, the medium was replaced with DMEM-high glucose containing 10% FBS, 1% PS and 10 μg/mL insulin, and then changed every two days. Nearly 90% of the cells have differentiated into mature adipocytes after 14 days of culture.

c. Protein Quantification Analysis:
  1. Following removal of culture medium, the cells were washed three times with PBS.
  2. Trypsin was added to dislodge the cells from culture plates and the cells were collected in the tube using PBS.
  3. Centrifugation at 2,000 rpm for 5 minutes, the supernatant was discarded and lysis buffer was added to lyse the cells.
  4. Centrifugation at 14,000 rpm for 10 minutes and the resulting supernatant was used as test sample. Bio-Rad Protein assay buffer was diluted 5 fold first and an aliquot of 900 μl diluted assay buffer was mixed homogenously with 100 μl supernatant or standard solution BSA and incubated for 5 minutes.
  5. Protein concentration was measured at $A_{595}$.

Oil Red O staining for measuring intracellular lipid droplets: Oil Red O is an oil soluble dye which stains lipids in cytoplasm in red.
  1. Remove the medium, and wash the cells three times with PBS.
  2. Add 200 μl methanol and incubate for 1 hour to fix the cells.
  3. Prepare oil red O working solution from oil red O stock solution, and add 2000 oil red O working solution to the washed cells and stain for 1 hr.
  4. Remove the dye and wash the cells 3 times with de-ionized water followed by removal of excess water.
  5. Observe and acquire the images of the cells under the microscope for analysis.
  6. Add 500 μl isopropanol and incubate overnight to dissolve the dye and measure OD at 492 nm. The oil amount of each cell is determined by dividing the measured oil amount with protein amount Test Results Lr263 cell lysate is prepared by sonication of the cells in PBS at the concentration of $1 \times 10^{10}$ cells/ml and the obtained lysates were then added to 3T3-L1 preadipocytes at various concentrations as treatments and the effect(s) of the cell lysates on lipid cell differentiation were subsequently examined.

Figure 1A:
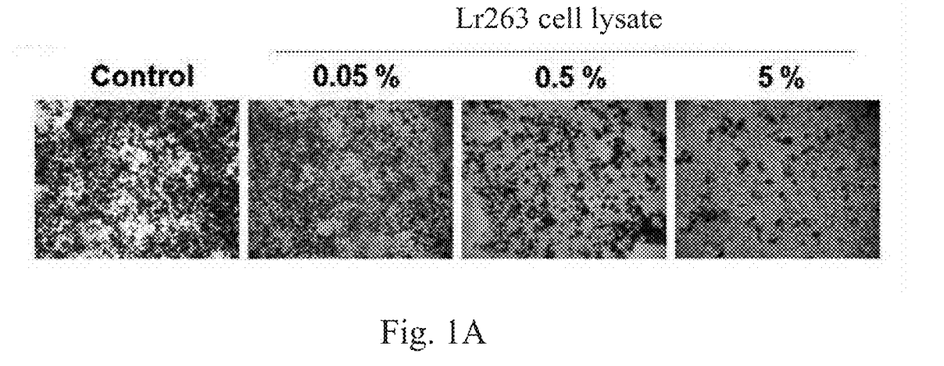
FIG. 1A shows the effects of Lr263 bacterial cell lysates on the oil content in adipocytes, visualized by Oil Red 0 staining (100× magnification).

After being cultured for 22 days, adipocytes were stained with Oil Red O and oil droplets were clearly visible under the microscope (red areas). From FIG. 1A, increase of the concentration of Lr263 cell lysates decreases the stained areas of red oil droplets.

Figure 1B:
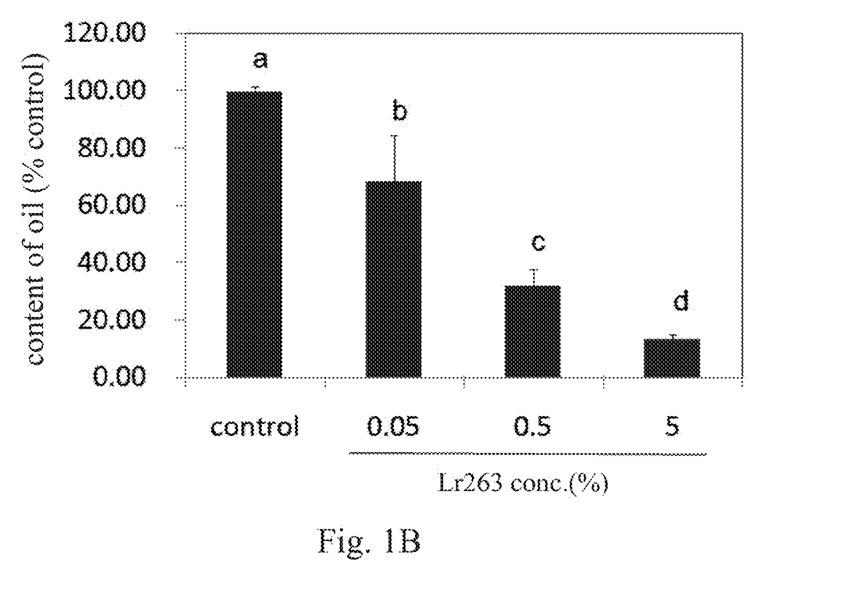
FIG. 1B shows the quantitative content of oil (%) from FIG. 1A, in triplicate test compared with the control group as 100%, and a, b and c represent significant difference were observed, $p<0.05$, by Duncan analysis.

The levels of oil droplets as well as inhibition of lipid biosynthesis after addition of 0.05 and 0.5% Lr263 cell lysates to fat cells were 68.5±16.0%/32.1±5.6% and 30%/70%, respectively, whereas treating the cells with the highest concentration of cell lysates at 5% only inhibits about 90% of lipid biosynthesis and the level of lipids is 13.4±1.6%(FIG. 1B).

In summary, Lr263 cell lysates can effectively inhibit formation of oil droplets during the process of adipocyte differentiation; in other words, it can inhibit biosynthesis of lipid.

Therefore, according to the results obtained from in vitro studies, Lr263 is a *Lactobacillus* strain which has the anti-obesity potential.

EXAMPLE 2

Experimental procedures: The rats were fed with high fat feeds and *Lactobacillus* bacteria from day 1 and were sacrificed after 12 weeks of feeding. During the course of the experiment, water as well as food intake were recorded every day, body weight and fasting blood glucose were documented every week, and oral glucose tolerance was examined every four weeks.

Preparation of the dead *Lactobacillus* bacteria: *Lactobacillus Reuteri* Lr263 bacteria were cultured in MRS broth in the 37° C. incubator for 12 hours followed by washing twice with PBS and then incubated in water bath at 100° C. for another 20 minutes before cryoprotectant was added. The Lr263 bacterial culture was freeze-dried into powder using a freeze dryer.

Detailed diet formulations of normal as well as high fat diets are described as follows:

TABLE 3

Diet formulations

| Ingredient (g/kg) | Normal Diet group | High Fat Diet (HFD) group |
|---|---|---|
| Casein | 200 | 232 |
| L-Cystine | 3.0 | 3.0 |
| DL-Methionine | — | 3.5 |
| Corn Starch | 397.48 | 137 |
| Maltodextrin | 132 | 150 |
| Sucrose | 100 | 162.58 |
| Cellulose | 50 | 50 |
| Cholesterol | — | 1.9 |
| Mineral Mix (AIN-93) | 35 | 40.60 |
| Calcium phosphate dibasic | — | 4.64 |
| Vitamin Mix (AIN-93) | 10 | 16.24 |
| Choline Bitartrate | 2.5 | 5 |
| tert-butylhydroquinone | 0.014 | 0.04 |
| Soybean oil | 70 | 40 |
| Lard | — | 153.5 |

Animal study: Male SD (Sprague-Dawley) rats at the age of five weeks old were purchased from BioLASCO Taiwan Co., Ltd. (Taipei, Taiwan). Throughout the experiment, the rats were housed in air-conditioned and temperature-adjusted plastic cages with a 12-h light/dark cycle and room temperature at 25±1° C. and have free access to water and food. The rats, based on their body weights, were randomly assigned to one of the eight groups as shown below after a week of adjustments.

1. Normal diet group:
    Fed with normal diet and 1 mlRO water everyday
2. Normal diet+Lr263 dead bacteria group:
    Fed with normal diet andLr263 bacteria ($5 \times 10^9$ cells/rat/per day) everyday
3. High fat diet (HFD)(negative control) group:
    Fed with HFD and 1ml RO water per day everyday
4. HFD+Shirota dead bacteria (positive control) group:
    Fed with normal diet and Shirota bacteria ($5 \times 10^9$ cells/rat/per day) every day. Professor Minoru Shirota, a microbiologist at the Department of Medicine, Kyoto University, Japan, successfully identified the lactic acid bacteria which is beneficial to human's gastrointestinal tract in 1930's and the strain was named *Lactobacillus casei* strain Shirota which is used as the positive control group in this application.
5. HFD+Lr263 dead bacteria low dose group:
    Fed with HFD and dead Lr263 bacteria ($5 \times 10^5$ cells/rat/per day) everyday
6. HFD+Lr263 dead bacteria medium dose group:
    Fed with HFD and dead Lr263 bacteria ($5 \times 10^7$ cells/rat/per day) everyday
7. HFD+Lr263 dead bacteria high dose group:
    Fed with HFD and dead Lr263 bacteria ($5 \times 10^9$ cells/rat/per day) everyday
8. HFD+Lr263 live bacteria group:
    Fed with HFD and Lr263 live bacteria ($2 \times 10^9$ cells/rat/per day) everyday Statistical analyses: Data collected was analyzed by one-way analysis of variance (ANOVA) using SPSS to determine the differences among these experimental groups. Where significant difference was observed ($P<0.01$), the data was subjected to Duncan's new multiple range test for further analysis.

Figure 2B:
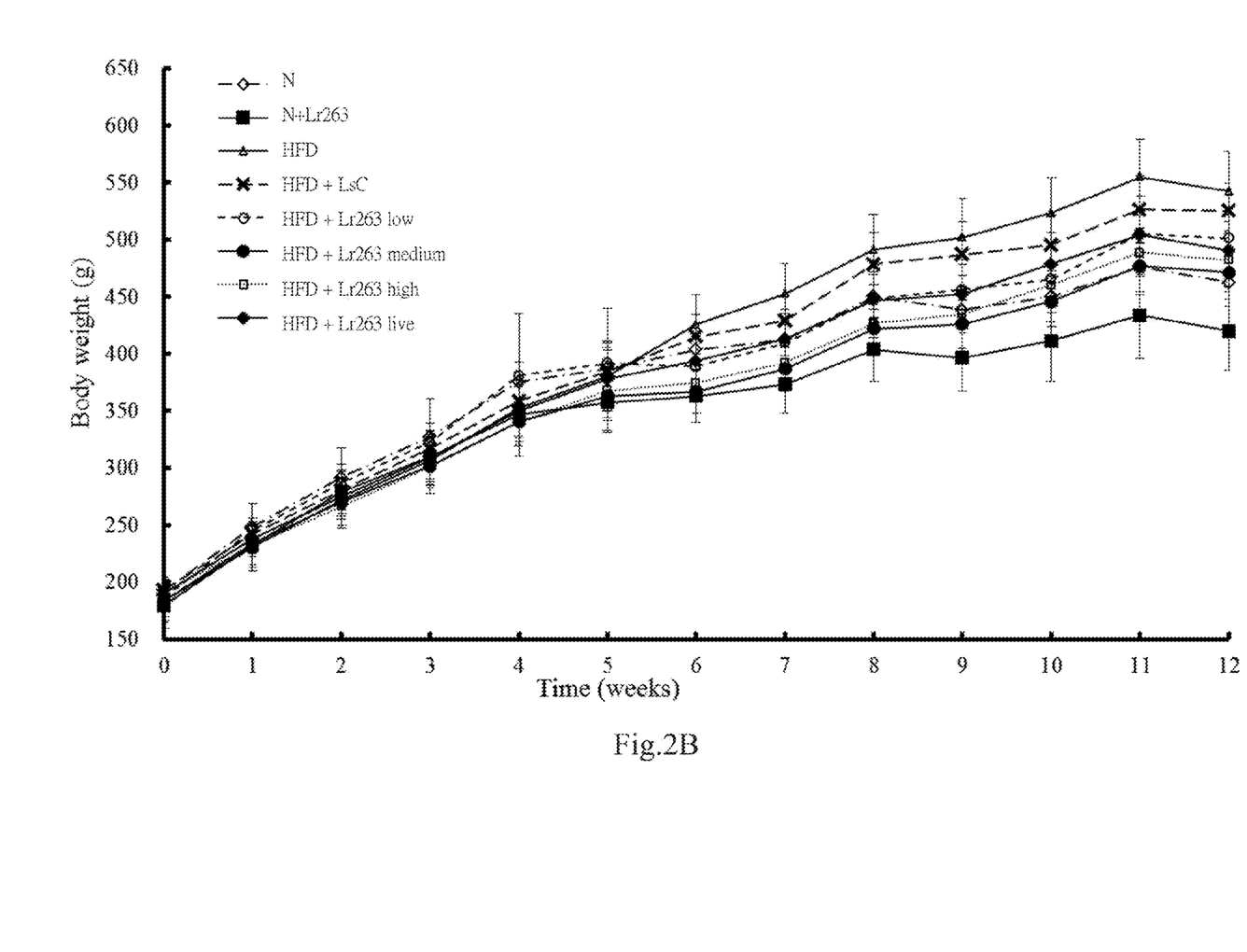
FIG. 2B shows the effect of Lr 263 bacteria on body weight between week 0 and week 12 in growth curve.

Test Results:

A. The Effect of Lr263 dead Bacteria on Body Weight:

Following feeding with different diets/treatments, at the end of week 12, only the body weight of the rats in the positive control HFD+Shirota group showed reduction; however, the decrease was not significant. On the contrary, rats fed with HFD+Lr263 dead bacteria low dose, HFD+Lr263 dead bacteria medium dose, HFD+Lr263 dead bacteria high dose and HFD+Lr263 live bacteria all demonstrated significant weight loss when compared with HFD group (FIG. 2A-B and Table 4). Moreover, HFD+Lr263 dead bacteria medium dose treatment has even better effect on lowering body weight than HFD+Lr263 live bacteria treatment, indicating both live and dead Lr263 bacteria are effective in treating obesity and reducing body weight.

Figure 3:
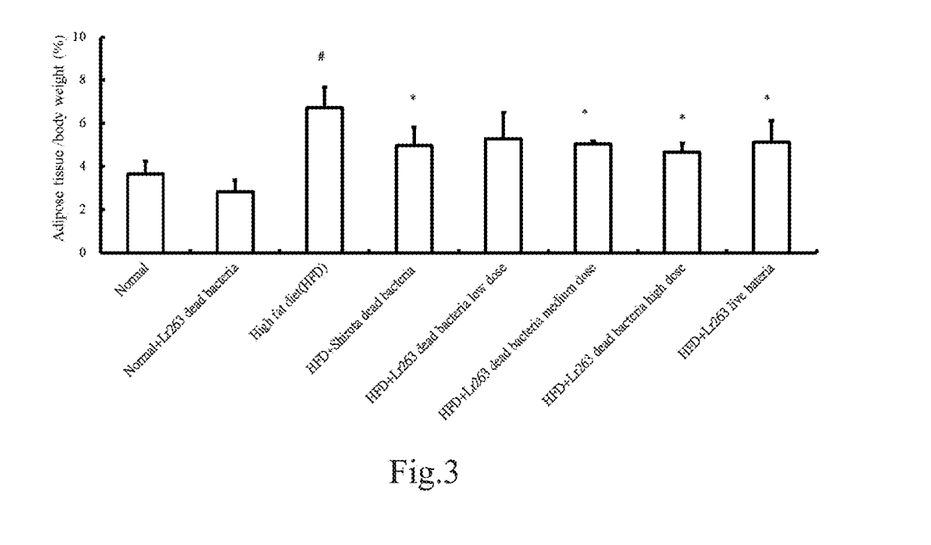
FIG. 3 shows the effects of Lr263 bacteria on the ratios of adipose tissue/body weight.

B. The Effect of Lr263 Bacteria on Total Adipose Tissues/Body Weight Ratio:

Following feeding with different diets/treatments, at the end of week 12, the adipose tissue/body weight ratios of HFD+Lr263 dead bacteria medium dose, HFD+Lr263 dead bacteria high dose and HFD+Lr263 live bacteria groups were all significantly lower than that of the HFD group (FIG. 3). In addition, the adipose tissue/body weight ratios of the rats fed with Lr263 dead bacteria had declined over the time, and the reduction rate of HFD+Lr263 dead bacteria low dose, HFD+Lr263 dead bacteria medium dose, HFD+Lr263 dead bacteria high dose groups were 21.6%, 24.8% and 31.0%, respectively, when compared with the HFD group.

Figure 4:
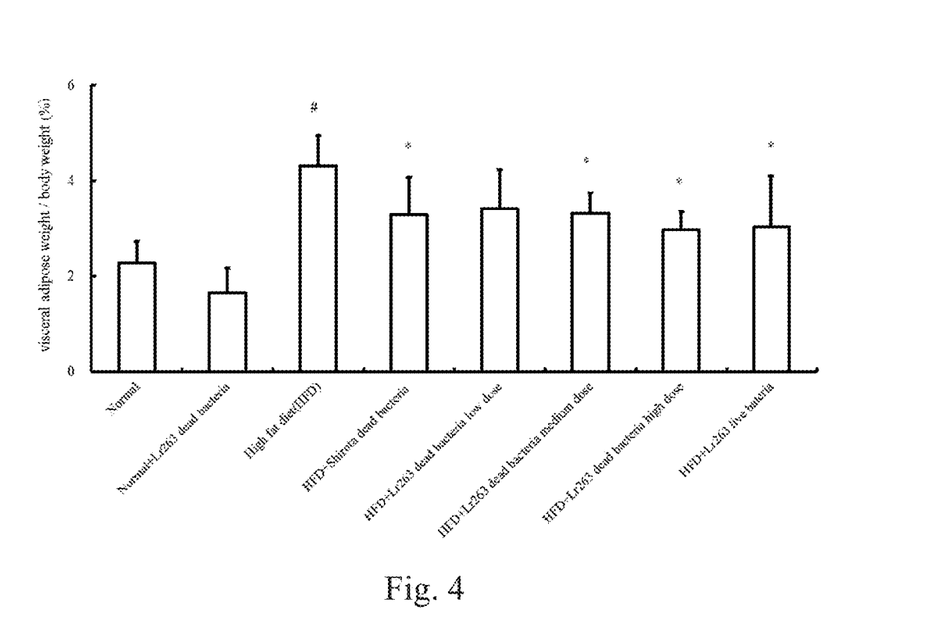
FIG. 4 shows the effects of Lr263 bacteria on the ratios of visceral adipose weight/body weight.

C. The Effect of Lr263 Bacteria on Visceral Fat/Body Weight Ratio:

Based on the abovementioned results of total adipose tissue/body weight ratios, the change of visceral fat was further examined at week 12. Similarly, the visceral fat/body weight ratios of HFD+Lr263 dead bacteria medium dose, HFD+Lr263 dead bacteria high dose and HFD+Lr263 live bacteria groups were significantly lower than that of the HFD group (FIG. 4). Also, the visceral fat/body weight ratios of the rats fed with dead Lr263 bacteria had declined over the time, and the reduction rates of HFD+Lr263 dead bacteria low dose, HFD+Lr263 dead bacteria medium dose, HFD+Lr263 dead bacteria high dose groups were 20.9%, 23.2% and 31%, respectively, when compared with the HFD group.

Figure 5:
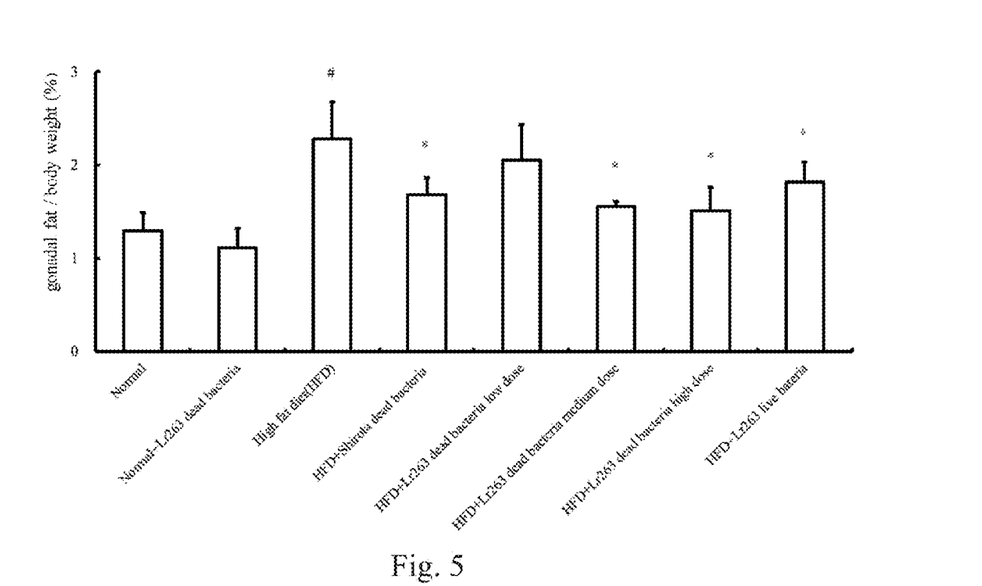
FIG. 5 shows the effects of Lr263 bacteria on the ratios of gonadal fat/body weight.

D. The Effect of Lr263 Bacteria on Gonadal Fat/Body Weight Ratio:

According to the abovementioned results of total adipose tissue/body weight ratios, the change of gonadal fat was further investigated at week 12. Likewise, the gonadal fat/body weight ratios of HFD+Lr263 dead bacteria medium dose, HFD+Lr263 dead bacteria high dose and HFD+Lr263 live bacteria groups were significantly lower than that of the HFD group (FIG. 5), and the gonadal fat/body weight ratios of the rats fed with dead Lr263 bacteria had declined over the time and the reduction rates of HFD+Lr263 dead bacteria low dose, HFD+Lr263 dead bacteria medium dose, HFD+Lr263 dead bacteria high dose groups were 10.0%, 31.8% and 33.7%, respectively, when compared with the HFD group.

Figure 6:
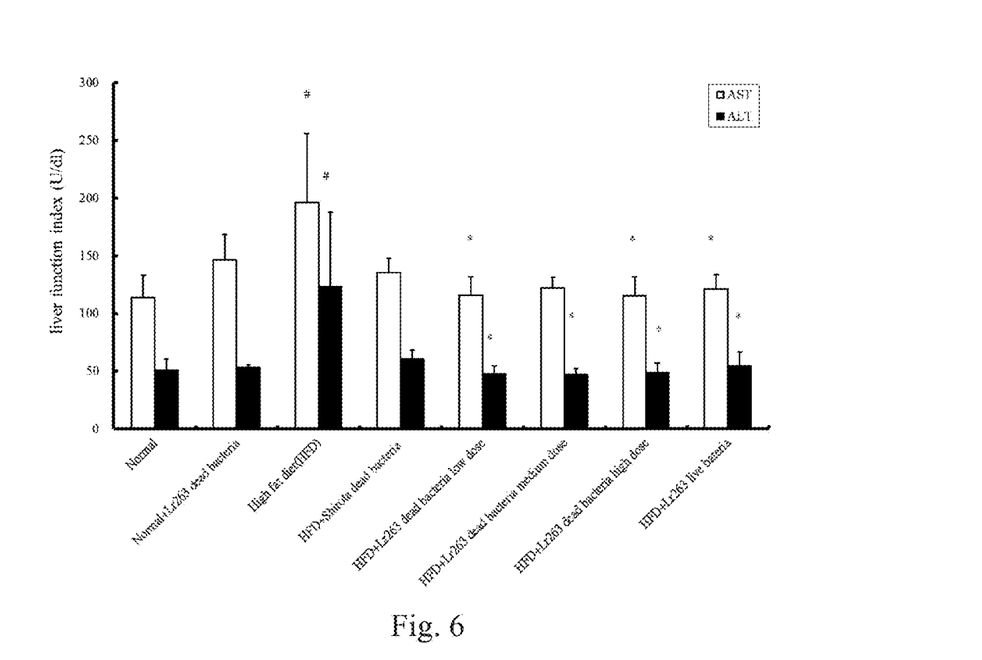
FIG. 6 shows the effects of Lr263 bacteria on liver function.

E. The Effect of Lr263 Bacteria on Liver Function:

Following feeding with different diets/treatments, serum AST (U/L) and ALT (U/L) each group was examined at the end of week 12. According to the results, serum AST levels were significantly lower in the HFD+Lr263 dead bacteria low dose, HFD+Lr263 dead bacteria high dose and HFD+Lr263 live bacteria groups than that of the HFD group (FIG. 6), whereas no significance was found in the HFD+Shirota group when compared with the HFD group. Furthermore, serum ALT levels are significantly lower in the groups of HFD+Lr263 dead bacteria low dose, HFD+Lr263 dead bacteria medium dose, HFD+Lr263 dead bacteria high dose and HFD+Lr263 live bacteria than that of the HFD group (FIG. 6), whereas no significance was found in the HFD+Shirota group when compared with the HFD group.

Unpredictably, dead Lr263 bacteria at low dose ($5 \times 10^5$ cells/rat/per day) can effectively lower serum AST as well as ALT levels and exert the same effects as obtained from the group fed with high dose of live Lr263 bacteria ($2 \times 10^9$ cells/rat/per day) and the results are even comparable to those observed in normal diet group.

Figure 7:
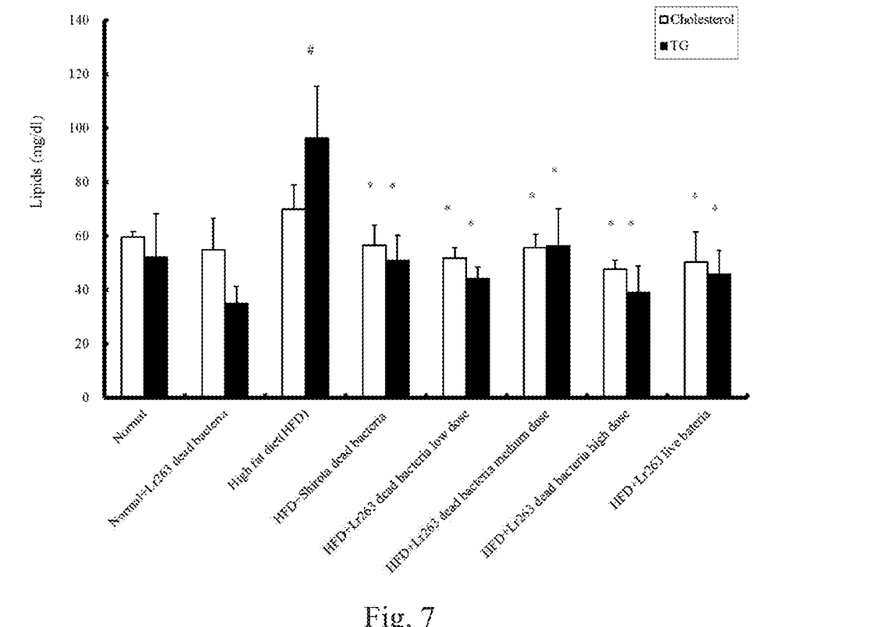
FIG. 7 shows the effects of Lr263 bacteria on lipid concentrations in blood.

F. The Effect of Lr263 Bacteria on Blood Lipid Levels:

Following feeding with different diets/treatments, the serum T-CHO (mg/dL) and TG (mg/dL) levels of each group were examined at the end of week 12. From the results, the concentrations of total cholesterol detected in the groups of HFD+Lr263 dead bacteria low dose, HFD+Lr263 dead bacteria medium dose, HFD+Lr263 dead bacteria high dose and HFD+Lr263 live bacteria were all significantly lower than that of the HFD group (FIG. 7). Likewise, triglyceride levels were also significantly lower in the HFD+Lr263 dead bacteria low dose, HFD+Lr263 dead bacteria medium dose, HFD+Lr263 dead bacteria high dose and HFD+Lr263 live bacteria groups when compared with the HFD group (FIG. 7).

Unexpectedly, dead Lr263 bacteria at low dose ($5 \times 10^5$ cell//rat/per day) can exert effects similar to those obtained from the group fed with normal diet.

Figure 8:
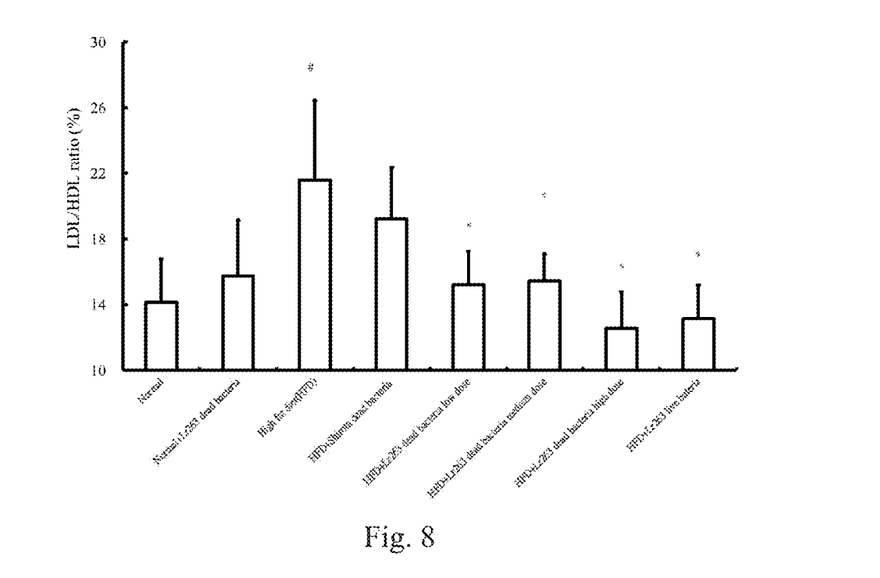
FIG. 8 shows the effects of Lr263 bacteria on LDL/HDL ratio.

G. The Effect of Lr263 Bacteria on LDL/HDL Ratios:

Following feeding with different diets/treatments, the LDL/HDL ratio of each group was measured at the end of week 12. According to the results, the LDL/HDL ratios were significantly lower in the groups of HFD+Lr263 dead bacteria low dose, HFD+Lr263 dead bacteria medium dose, HFD+ Lr263 dead bacteria high dose and HFD+Lr263 live bacteria than that of the HFD group (FIG. 8), whereas no significance was found in the HFD+Shirota group when compared with the HFD group.

Surprisingly, we found that feeding with low dose of dead Lr263 bacteria ($5 \times 10^5$ cells//rat/per day) has almost the same effect as feeding with normal diet and the LDL/HDL ratio decreased more significantly with the increase of the bacterial dosage.

EXAMPLE 3

Following the previously described experiment, since the effect of losing weight can be achieved through both live bacteria and dead, the efficiency between live bacteria and dead bacteria is to be compared by the following experiment.

In the instant example, the materials and methods is identical to the experiment presented in example 2 except the feature below:

Animal study: Male SD (Sprague-Dawley) rats at the age of five weeks old were purchased from BioLASCO Taiwan Co., Ltd. (Taipei, Taiwan). Throughout the experiment, the rats were housed in air-conditioned and temperature-adjusted plastic cages with a 12-h light/dark cycle and room temperature at 25±1° C. and have free access to water and food. The rats, based on their body weights, were randomly assigned to one of the 4 groups as shown below after a week of adjustments.

1. Normal diet group:
   Fed with normal diet and 1 ml RO water everyday
2. High fat diet (HFD)(negative control) group:
   Fed with HFD and 1 ml RO water per day everyday
3. HFD+Lr263 dead bacteria group:
   Fed with HFD and Lr263 bacteria ($2 \times 10^9$ cells/rat/per day) everyday
4. HFD+Lr263 live bacteria group:
   Fed with HFD and dead Lr263 bacteria ($2 \times 10^9$ cells/rat/per day) everyday Data were collected and analyzed by standardizing by HFD rat body weight and body fat. The results are presented in Table. 6, 7. After 8 weeks experiment, the body weight and body fat of HFD rats were increased compared to normal diet group (p<0.05). In contrast, the body weight and body fat of the rats which were fed with live or dead bacteria Lr263 significantly decrease compared to HFD group (p<0.05). Moreover, the efficiency of lowering weight and fat is better treating with dead bacteria than live bacteria.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

TABLE 4

The body weight (g) of rats measured between week 1 and 12 after feeding with Lr263 bacteria

| | 0 | 1 | 2 | 3 | 4 | 5 | 6 |
|---|---|---|---|---|---|---|---|
| Normal diet | 192.750 ± 9.020 | 248.125 ± 8.149 | 291.375 ± 11.880 | 327.375 ± 11.831 | 375.250 ± 17.831 | 387.000 ± 22.418 | 403.833 ± 12.497 |
| Normal diet + Lr263 dead bacteria | 179.500 ± 20.213 | 232.250 ± 19.271 | 279.125 ± 19.060 | 310.125 ± 22.267 | 346.625 ± 25.895 | 357.250 ± 25.672 | 363.167 ± 23.404 |
| High fat diet (HFD) | 183.875 ± 18.917 | 231.000 ± 21.507 | 271.875 ± 24.625 | 307.000 ± 24.791 | 352.000 ± 28.455 | 380.625 ± 30.771 | 425.667 ± 25.997 |

TABLE 4-continued

The body weight (g) of rats measured between week 1 and 12 after feeding with Lr263 bacteria

| | | | | | | | |
|---|---|---|---|---|---|---|---|
| HFD + Shirota dead bacteria | 193.125 ± 6.357 | 242.375 ± 6.255 | 280.250 ± 10.430 | 317.000 ± 12.862 | 358.750 ± 14.849 | 384.500 ± 18.815 | 415.000 ± 19.246 |
| HFD + Lr263 dead bacteria low dose | 186.800 ± 17.061 | 245.300 ± 23.185 | 286.700 ± 31.202 | 322.900 ± 38.197 | 380.900 ± 54.490 | 391.800 ± 47.893 | 389.167 ± 25.949 |
| HFD + Lr263 dead bacteria medium dose | 183.400 ± 16.801 | 234.200 ± 18.600 | 270.100 ± 20.851 | 301.700 ± 23.847 | 340.700 ± 30.576 | 363.100 ± 30.661 | 367.000 ± 18.730 |
| HFD + Lr263 dead bacteria high dose | 191.000 ± 7.803 | 232.800 ± 7.584 | 266.100 ± 8.863 | 301.000 ± 15.706 | 340.400 ± 21.454 | 367.600 ± 26.171 | 374.500 ± 10.766 |
| HFD + Lr263 live bacteria | 190.000 ± 10.625 | 238.111 ± 12.713 | 275.111 ± 17.230 | 309.333 ± 18.921 | 350.222 ± 22.515 | 377.889 ± 27.652 | 393.833 ± 23.920 |

| | 7 | 8 | 9 | 10 | 11 | 12 |
|---|---|---|---|---|---|---|
| Normal diet | 412.500 ± 16.861 | 450.333 ± 19.107 | 438.667 ± 20.334 | 450.167 ± 22.400 | 476.167 ± 21.535 | 462.500 ± 20.849 |
| Normal diet + Lr263 dead bacteria | 373.500 ± 25.122 | 403.833 ± 27.953 | 396.667 ± 29.857 | 411.167 ± 35.358 | 433.667 ± 37.724 | 420.167 ± 34.557 |
| High fat diet (HFD) | 452.500 ± 26.786[#] | 491.333 ± 30.852[#] | 502.167 ± 33.683[#] | 523.333 ± 30.612[#] | 555.000 ± 33.100[#] | 542.667 ± 34.932[#] |
| HFD + Shirota dead bacteria | 429.000 ± 20.248 | 478.500 ± 27.848 | 487.000 ± 28.914 | 495.500 ± 25.805 | 526.333 ± 29.460 | 525.333 ± 23.956 |
| HFD + Lr263 dead bacteria low dose | 409.167 ± 26.248 | 448.500 ± 26.972* | 456.167 ± 22.194* | 465.167 ± 29.027* | 505.167 ± 20.634* | 501.500 ± 14.694* |
| HFD + Lr263 dead bacteria medium dose | 387.167 ± 19.682 | 422.167 ± 21.236* | 426.000 ± 21.119* | 445.833 ± 22.040* | 477.000 ± 25.448* | 471.167 ± 23.473* |
| HFD + Lr263 dead bacteria high dose | 392.333 ± 13.231 | 426.667 ± 12.501* | 434.833 ± 12.859* | 460.167 ± 18.723* | 489.000 ± 21.457* | 482.167 ± 23.912* |
| HFD + Lr263 live bacteria | 413.000 ± 25.915 | 447.000 ± 24.844* | 452.333 ± 30.323* | 478.500 ± 27.970* | 504.000 ± 34.624* | 490.600 ± 31.556* |

[#] $p < 0.05$ data is statistically significant when compared with normal diet group
* $p < 0.05$ data is statistically significant when compared with HFD group

TABLE 5

The body weight, fat ratio and serum biochemical analysis results measured after feeding Lr263 for 12 weeks

| | Normal diet | Normal diet + Dead Lr263 | High fat diet (HFD) | HFD + Dead Shirota |
|---|---|---|---|---|
| Body weight (g) | 462.500 ± 20.849 | 420.167 ± 34.557 | 542.667 ± 34.932 | 525.333 ± 23.956 |
| Total adipose tissue/ Body weight (%) | 3.651 ± 0.610 | 2.819 ± 0.554 | 6.733 ± 0.941[#] | 4.975 ± 0.843* |
| Weight of visceral fat/ Body weight (%) | 2.287 ± 0.444 | 1.654 ± 0.518 | 4.320 ± 0.642[#] | 3.294 ± 0.774* |
| Weight of gonadal fat/ Body weight (%) | 1.293 ± 0.197 | 1.116 ± 0.204 | 2.278 ± 0.397[#] | 1.681 ± 0.181* |
| Aspartate aminotransferase (AST)(U/L) | 113.983 ± 19.186 | 146.367 ± 22.128 | 196.050 ± 60.014[#] | 135.517 ± 12.464 |
| Alanine aminotransferase (ALT)(U/L) | 51.133 ± 9.573 | 53.250 ± 2.134 | 123.350 ± 64.353[#] | 60.533 ± 7.783 |
| T-CHO (mg/dL) | 59.525 ± 2.076 | 54.767 ± 11.810 | 69.767 ± 9.209 | 56.500 ± 7.272* |
| TG (mg/dL) | 52.167 ± 16.018 | 34.983 ± 6.225 | 96.267 ± 19.048[#] | 50.967 ± 9.148* |

TABLE 5-continued

The body weight, fat ratio and serum biochemical analysis results measured after feeding Lr263 for 12 weeks

|  | Normal diet | Normal diet + Dead Lr263 | High fat diet (HFD) | HFD + Dead Shirota |
|---|---|---|---|---|
| LDL/HDL (%) | 14.124 ± 2.656 | 15.738 ± 3.436 | 21.596 ± 4.865# | 19.221 ± 3.139 |

|  | HFD + Low dose dead Lr263 | HFD + Medium dose dead Lr263 | HFD + High dose dead Lr263 | HFD + Live Lr263 |
|---|---|---|---|---|
| Body weight (g) | 501.500 ± 14.694* | 471.167 ± 23.473* | 482.167 ± 23.912* | 490.600 ± 31.556* |
| Total adipose tissue/Body weight (%) | 5.282 ± 1.229 | 5.061 ± 0.110* | 4.647 ± 0.423* | 5.121 ± 1.001* |
| Weight of visceral fat/Body weight (%) | 3.417 ± 0.824 | 3.317 ± 0.430* | 2.979 ± 0.381* | 3.039 ± 1.059* |
| Weight of gonadal fat/Body weight (%) | 2.052 ± 0.384 | 1.554 ± 0.055* | 1.510 ± 0.252* | 1.819 ± 0.215* |
| Aspartateaminotransferase (AST)(U/L) | 115.850 ± 15.880* | 122.133 ± 9.126 | 115.367 ± 16.262* | 121.225 ± 12.265* |
| Alanineaminotransferase (ALT)(U/L) | 47.733 ± 6.753* | 47.383 ± 5.064* | 48.667 ± 8.339* | 54.720 ± 11.876* |
| T-CHO (mg/dL) | 51.617 ± 3.992* | 55.700 ± 4.875* | 47.633 ± 3.307* | 50.300 ± 11.081* |
| TG (mg/dL) | 44.100 ± 4.408* | 56.417 ± 13.582* | 39.033 ± 9.734* | 45.883 ± 8.695* |
| LDL/HDL (%) | 15.211 ± 2.021* | 15.430 ± 1.659* | 12.543 ± 2.212* | 13.142 ± 2.034* |

*$p < 0.05$ data is statistically significant when compared with HFD group

TABLE 6

The body weight (g) and body fat of rats measured after feeding with Lr263 bacteria for 8 weeks

| Group | Normal | High fat diet (HFD) | HFD + live Lr263 | HFD + dead Lr263 |
|---|---|---|---|---|
| Body weight (g) | 462.5 ± 20.85 | 542.67 ± 34.93 # | 490.6 ± 31.56* | 452.86 ± 27.9* |
| Body fat (%) | 3.65 ± 0.61 | 6.73 ± 0.94 # | 5.12 ± 1.00* | 4.26 ± 0.3* |

: $p > 0.05$ data is statistically significant when compared with normal diet group
: $p > 0.05$ compared with Normal group
*$p > 0.05$ compared with HFD group

TABLE 7

The percentage of decreasing of body weight (g) and body fat of rats in table 6

| Group | HFD ± live Lr263 | HFD ± dead Lr263 |
|---|---|---|
| Body weight (g) | −9.6% | −18.0% |
| Body fat (%) | −23.9% | −33.3% |

What is claimed is:

1. A method used for reducing body weight of a high fat diet subject, comprising administrating a probiotic composition, wherein the probiotic bacterial strain includes *Lactobacillus reuteri* GMNL-263 with the deposition number of CCTCC M 209263, wherein the composition comprises dead bacteria and the dosage of composition is between $5 \times 10^5$ and $2 \times 10^9$ cells/day.

2. The method as recited in claim 1, wherein the composition is a pharmaceutical composition, food or their combinations thereof.

3. The method as recited in claim 2, wherein the pharmaceutical composition may further comprise a pharmaceutically acceptable vehicle.

4. The method as recited in claim 2, wherein the pharmaceutical composition is prepared in a dosage form for oral administration.

5. The method as recited in claim 4, wherein the dosage form is selected from group consisting of solution, suspension, emulsion, powder, tablet, pill, syrup, lozenge, troche, chewing gum, slurry, capsule.

6. The method as recited in claim 2, wherein the food further comprise at least one of the probiotic bacterial strains selected form the group consisting of *Lactobacillus* sp., *Bifidobacterium* sp., *Streptococcus* sp. and yeasts.

7. The method as recited in claim 2, wherein the food further comprise an edible material and the edible material comprise water, fluid milk products, milk, concentrated milk, fermented milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jelly, candies, infant formulas, health foods, animal feeds, Chinese herbs or dietary supplements.

8. A method of the treatment of obesity and its complications for a high fat diet subject, comprising administrating a probiotic composition, wherein the probiotic bacterial strain includes *Lactobacillus reuteri* GMNL-263 with the deposition number of CCTCC M 209263, wherein the composition comprises dead bacteria and the dosage of composition is between $5 \times 10^5$ and $\times 10^9$ cells/day.

9. The method as recited in claim 8, wherein the complications are selected from the groups consisting of hyperlipidemia, atherosclerosis, coronary heart disease and fatty liver.

10. A method of the treatment of inhibition of the biosynthesis of lipids, high total body fat, high visceral fat, high gonadal fat, high total cholesterol, high triglyceride concentration, or high LDL/HDL ratio for a high fat diet subject, comprising administrating a probiotic composition, wherein the probiotic bacterial strain includes *Lactobacillus reuteri*

GMNL-263 with the deposition number of CCTCC M 209263, wherein the composition comprises dead bacteria and the dosage of composition is between $5 \times 10^5$ and $2 \times 10^9$ cells/day.

* * * * *